United States Patent
Su et al.

(10) Patent No.: US 10,463,645 B2
(45) Date of Patent: Nov. 5, 2019

(54) METHOD FOR DELAYING THE ONSET OF PULMONARY FIBROSIS OR TREATING PULMONARY FIBROSIS

(71) Applicant: EVERFRONT BIOTECH INC., New Taipei (TW)

(72) Inventors: Hong-Lin Su, Taichung (TW);
Shinn-Zong Lin, Taichung (TW);
Horng-Jyh Harn, New Taipei (TW);
Tzyy-Wen Chiou, Hualien (TW);
Hong-Meng Chuang, New Taipei (TW)

(73) Assignee: EVERFRONT BIOTECH INC., New Taipei (TW)

( * ) Notice: Subject to any disclaimer, the term of this patent is extended or adjusted under 35 U.S.C. 154(b) by 10 days.

(21) Appl. No.: 15/593,910

(22) Filed: May 12, 2017

(65) Prior Publication Data
US 2017/0333391 A1    Nov. 23, 2017

Related U.S. Application Data

(60) Provisional application No. 62/338,787, filed on May 19, 2016.

(51) Int. Cl.
*A61K 31/34* (2006.01)
*A61K 31/19* (2006.01)
(Continued)

(52) U.S. Cl.
CPC .......... *A61K 31/365* (2013.01); *A61K 31/192* (2013.01)

(58) Field of Classification Search
CPC ............................ A61K 31/192; A61K 31/343
(Continued)

(56) References Cited

U.S. PATENT DOCUMENTS 7,744,890 B2 * 6/2010 Nichols ............ A61K 39/39591
424/177.1
2014/0045765 A1 * 2/2014 Lin ...................... A61K 31/365
514/17.9

FOREIGN PATENT DOCUMENTS

WO    WO 2006125651 A2 * 11/2006 ........... A61K 31/343

OTHER PUBLICATIONS

Wei-min, et al., Medical Journal of Wuhan University, vol. 22, No. 4, Oct. 2001 (abstract).*

(Continued)

*Primary Examiner* — Shengjun Wang
(74) *Attorney, Agent, or Firm* — Ping Wang; Morris, Manning & Martin, LLP

(57) ABSTRACT

The present invention relates to a method of delaying the onset of pulmonary fibrosis or treating pulmonary fibrosis, comprising administering to a subject in need an effective amount of an active ingredient selected from the group consisting of a compound of formula (I), a pharmaceutically acceptable salt of the compound of formula (I), and combinations thereof:

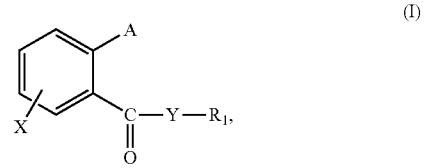

(I)

wherein,
A is a C5 alkyl or alkenyl optionally substituted with —OH or =O;
X is H or OH;

(Continued)

Y is O; and

R$_1$ is H or absent, with the proviso that, when R$_1$ is absent, Y and A bind together to form a five-membered ring.

18 Claims, 8 Drawing Sheets

(51) Int. Cl.
*A61K 31/365* (2006.01)
*A61K 31/192* (2006.01)

(58) Field of Classification Search
USPC .................................................. 514/570, 473
See application file for complete search history.

(56) References Cited

OTHER PUBLICATIONS

Mis, et al., Molecular and Cellular Neuroscience, 72 (2016), pp. 84-90.*
Zhong, et. al., Chin J. Prev Med. Mar. 2007, vol. 41, No. 2, pp. 105-109.*
Yang et al., Mol. BioSyst. 2012, 8. pp. 1789-1797.*
Whitsett, et. al., American Journal of Respiratory and Critical Care Medicine, vol. 184, 2011, pp. 401-406.*
Barnes et al. "Chronic obstructive pulmonary diseases: molecular and cellular mechanisms," Eur. Respir. J. 2003, vol. 22, pp. 672-688 (Year: 2003).*
Chao et al. Bioactivities of major constituents isolated from Angelica sinensis (Danggui), Chinese Medicine, 2011, vol. 6:29 (Year: 2011).*
Nakayama, S. et al., "Pirfenidone inhibits the expression of HSP47 in TGF-β1-stimulated human lung fibroblasts", Life Sciences, Jan. 16, 2008; 82(3-4), pp. 210-217.
Ashcroft, T. et al., "Simple method of estimating severity of pulmonary fibrosis on a numerical scale", J. Clin. Pathol., Apr. 1988, 41(4), pp. 467-470.

* cited by examiner

METHOD FOR DELAYING THE ONSET OF PULMONARY FIBROSIS OR TREATING PULMONARY FIBROSIS

CROSS REFERENCE TO RELATED APPLICATIONS

This application claims priority from U.S. Provisional Application Ser. No. 62/338,787 filed on May 19, 2016 with the United States Patent and Trademark Office, the disclosures of which are incorporated herein in their entirety by reference.

FIELD OF THE INVENTION

The present invention relates to a method of delaying the onset of pulmonary fibrosis or treating pulmonary fibrosis, comprising administering to a subject in need an effective amount of an active ingredient selected from the group consisting of a compound of formula (I), a pharmaceutically acceptable salt of the compound of formula (I), and combinations thereof:

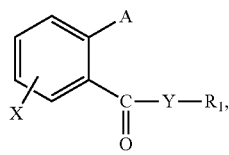

wherein,
A is a C5 alkyl or alkenyl optionally substituted with —OH or =O;
X is H or OH;
Y is O; and
$R_1$ is H or absent, with the proviso that, when $R_1$ is absent, Y and A bind together to form a five-membered ring.

BACKGROUND OF THE INVENTION

Pulmonary fibrosis (which is also called interstitial lung disease) refers to a disease that produces scar-like tissue in pulmonary interstices by accumulating extracellular matrix (ECM) components such as collagen, elastin and fibronectin in pulmonary interstitial tissue. Pulmonary fibrosis makes pulmonary tissue, which is originally as soft as a sponge, becomes as hard as concrete and thus loses elasticity, resulting in a gradually loss of the capabilities to contract, relax and exchange gas.

Generally, patients at an early stage of pulmonary fibrosis will have symptoms such as hyperpnoea, chest tightness and pain, cough, etc. However, those early stage symptoms are not easy to identify. Therefore, more than 50% of the pulmonary fibrosis patients have been misdiagnosed with asthma, emphysema, chronic obstructive pulmonary disease (COPD), or heart diseases. When definitely diagnosed, most of the pulmonary fibrosis patients' pulmonary functions have already decreased, and those patients also have the symptom of dyspnea, leading to chronic hypoxia. When the body lacks oxygen, attention and memory will decrease, and in addition, insufficient oxygen lead to cell weakness, physical function decline, slow metabolism, increased aging, various complications, etc. As for patients with late-stage pulmonary fibrosis, they can have heart failure and respiratory failure caused by long-term hypoxia, and even need to depend on inhaling air with a high concentration of oxygen to maintain life when the disease becomes severe.

The mortality rate of the pulmonary fibrosis patients is much higher than that of cancer patients. According to statistics, patients with pulmonary fibrosis have a five-year survival rate less than 50%, and a ten-year survival rate less than 10%. There is still a lack of medicaments that can effectively treat pulmonary fibrosis. The commercially available medicament, Pirfenidone (product name: Esbriet®), can improve the lung capacity of pulmonary fibrosis patients, but it does not have significant benefits on treating pulmonary fibrosis. Besides, Pirfenidone may produce various side-effects, such as nausea, emesis, dyspepsia, anorexia, erythematous rash, dizziness, photosensitivity, etc. Therefore, in clinic practice, there is still a need of a medicament that can delay the onset of pulmonary fibrosis and/or treat pulmonary fibrosis.

The inventors of the present invention found that the compound of formula (I) has the effects of enhancing the anti-oxidation capability of alveolar cells, increasing the survival rate of alveolar cells, alleviating oxidative stress-induced injury to the pulmonary tissue, inhibiting pulmonary fibroblast to myofibroblast conversion, inhibiting the epithelial-mesenchymal transition (EMT) of pulmonary fibroblasts and inhibiting the overexpression of extracellular matrix. Moreover, the compound of formula (I) can effectively regulate the immune response in pulmonary tissue, alleviate the thickening of alveolar wall tissue, alleviate the abnormal infiltration of pulmonary cells and/or alleviate the decrease in pulmonary function; thus it can be used to delay the onset of pulmonary fibrosis and/or treat pulmonary fibrosis.

SUMMARY OF THE INVENTION

An objective of the present invention is to provide a use of an active ingredient selected from the group consisting of a compound of formula (I), a pharmaceutically acceptable salt of the compound of formula (I), and combinations thereof, in the manufacture of a medicament for delaying the onset of pulmonary fibrosis and/or treating pulmonary fibrosis:

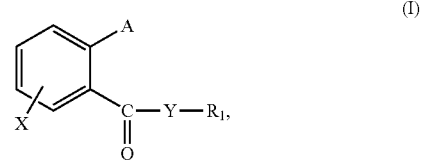

wherein, A is a C5 alkyl or alkenyl optionally substituted with —OH or =O; X is H or OH; Y is O; and $R_1$ is H or absent, with the proviso that, when $R_1$ is absent, Y and A bind together to form a five-membered ring.

In a preferred embodiment of the use according to the present invention, in the compound of formula (I), A is

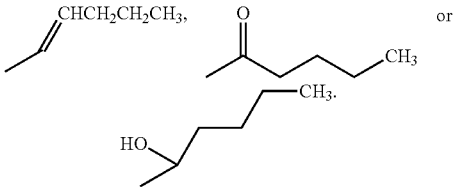

In another preferred embodiment of the use according to the present invention, in the compound of formula (I), A is

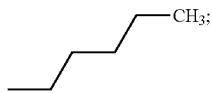

X is OH.

In still another preferred embodiment of the use according to the present invention, the compound of formula (I) is at least one of the following compound (1) and (2):

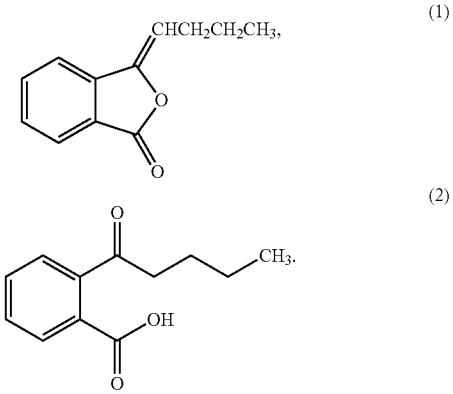

Another objective of the present invention is to provide a method of delaying the onset of pulmonary fibrosis or treating pulmonary fibrosis, comprising administering to a subject in need an effective amount of an active ingredient selected from the group consisting of the compound of formula (I) as mentioned above, a pharmaceutically acceptable salt of the compound of formula (I), and combinations thereof.

The detailed technology and some particular embodiments implemented for the present invention are described in the following paragraphs for people skilled in this field to well appreciate the features of the claimed invention.

BRIEF DESCRIPTION OF THE DRAWINGS

FIG. 8A is a bar diagram showing respiratory rate (RR) and accumulated volume (AV), FIG. 8B is a bar diagram showing tidal volume (TV) and relaxation time (RT), FIG. 8C is a bar diagram showing peak inspiratory flow (PIF) and peak expiratory flow (PEF), FIG. 8D is a bar diagram showing inspiratory time (Ti) and expiratory time (Te), and all of the FIGS. 8A-8D include the results of the control group, low-dose group, high-dose group and oil group;

DESCRIPTION OF THE PREFERRED EMBODIMENTS

Figure 1:
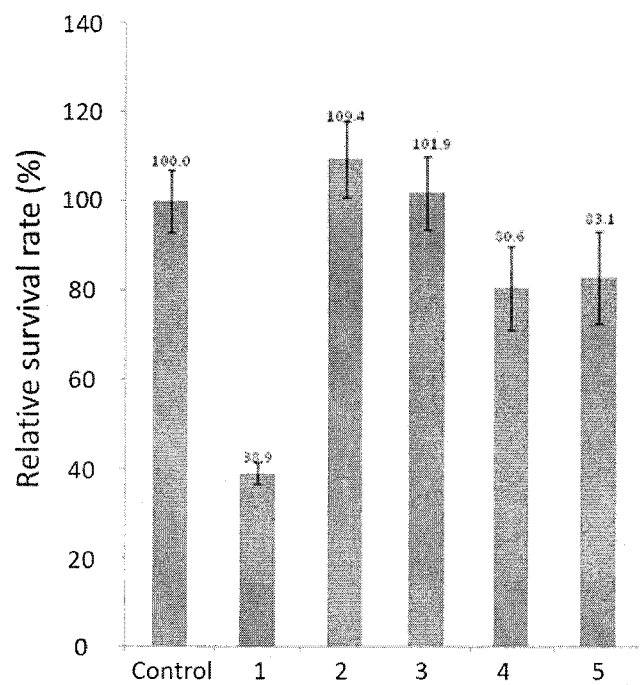
FIG. 1 is a bar diagram showing the survival rates of alveolar cells cultured in different mediums, wherein the control group was cultured in a F-12K medium, group 1 was cultured in a F-12K medium containing $H_2O_2$ (0.1 mM), group 2 was cultured in a F-12K medium containing $H_2O_2$ (0.1 mM) and compound (1) (5 μg/ml), group 3 was cultured in a F-12K medium containing $H_2O_2$ (0.1 mM) and n-acetylcysteine (NAC; 2 mM), group 4 was cultured in a F-12K medium containing $H_2O_2$ (0.2 mM) and compound (1) (5 μg/ml), and group 5 was cultured in a F-12K medium containing $H_2O_2$ (0.2 mM) and NAC (2 mM)

Some particular embodiments according to the present invention are described in the following paragraphs. However, the present invention may be realized in various embodiments without departing from the spirit of the present invention, and the present invention should not be considered to be limited to the embodiments described in the specification. In addition, unless otherwise state herein, the expressions "a," "the" or the like recited in the specification of the present invention (especially in the claims) should include both the singular and plural forms. The term "treat" or "treating" should not be considered as referring to treat a subject until it completely recovered, but should include maintaining the onset or disorder of the disease in a substantially static state, increasing the recovery rate of a subject, alleviating the severity of a particular condition, and increasing the life quality of a subject. Furthermore, the term "an effective amount" used in this specification refers to the amount of the compound that can at least partially alleviate the condition that is being treated in a suspected subject when administered to the subject. The term "subject" refers to a mammalian, including human and non-human animals.

The numerical ranges (e.g., 3 to 90) used in this specification should be construed as including all of the rational numbers in the ranges (e.g., 3, 3.1, 6, 6.5, 7, 7.9, 8, 9, 10, 20, 30, 40, 50, 60, 70, 80 and 90) and ranges consisting of any rational numbers in the ranges (e.g., 3.1 to 8, 10 to 60.5, 5.8 to 70.9 and 15 to 90). Therefore, the numerical ranges used in this specification should include all the possible combinations of numerical values between the lowest value and the highest value listed therein. In addition, the word "about", "approximately" or "almost" as used herein substantially represents values within ±20% of the stated value, preferably within ±10% and more preferably within ±5%.

In the present specification, when other external documents or other information sources are cited, it is generally for the purpose of providing the description of the background for the technical features of the present invention. Therefore, unless otherwise state herein, such citations of the external documents are not an admission that any or all of these documents or information sources form part of the prior art or are general knowledge in the art in any authority.

It has been pointed out by research that pulmonary fibrosis may relate to immune response, inflammation, stimulation caused by allogene, dysphagia, gastroesophageal reflux, etc. There is also related research that roughly divides the causes of pulmonary fibrosis into idiopathic, primary, immunity, medicinal, physical, etc., including pulmonary fibrosis caused by cryptogenic fibrosing alveolitis (CFA), usual interstitial pneumonia (UIP) and interstitial lung disease (ILD).

For example, when immune overreaction occurs in the lungs, the macrophages in the tissue will be abnormally activated and then release transforming growth factor β (TGF-β) and interleukin, and thus attracts neutrocytes to the pulmonary tissue. The neutrocytes then release oxide radicals, resulting in injury to the pulmonary tissue. In response to this pulmonary tissue injury, cells in the tissue will secrete extracellular matrix components such as collagen, elastin and fibronectin to repair the tissue. However, oversecretion of the extracellular matrix components can cause pulmonary fibrosis. The above description can be seen in, for example, Life Sci. 2008 Jan. 16; 82(3-4): 210-7, which is entirely incorporated herein for reference.

It has been proven by research that, in the process of the development of pulmonary fibrosis, the activation of transforming growth factor β (TGF-β)/drosophila mothers against decapentaplegic protein family (Smad) signaling pathway will induce the epithelial-mesenchymal transition (EMT) of pulmonary fibroblast, and it will also stimulate fibroblasts to proliferate and convert into myofibroblasts. When the pulmonary fibroblasts perform the epithelial-mesenchymal transition (EMT), the polarity between the cells gradually diminishes and the migration ability of the cells increases, and thus the cells are more easily to creep and invade, leading to the cells being involved in the fibrosis of tissue. Furthermore, a myofibroblast is a kind of cell that expresses alpha smooth muscle actin (α-SMA) marker protein and has a high migration ability. Myofibroblast in the lungs will secrete an excessive amount of extracellular matrix components such as collagen, elastin and fibronectin after it is activated, and those extracellular matrix components will accumulate in the pulmonary interstitial tissue to form the microenvironment of pulmonary fibrosis, and thus induces the contraction in the intercellular substance, forming scar tissue.

It has been proven that bone morphogenetic protein-7 (BMP-7) can inhibit the activation of the TGF-β/Smad signaling pathway. Therefore, if the expression of BMP-7 can be increased, it is helpful for the inhibition of the TGF-β/Smad signaling pathway, and thus achieves the effect of delaying the onset of pulmonary fibrosis.

As described above, the occurrence of pulmonary fibrosis closely relates to the pulmonary immune overreaction and the epithelial-mesenchymal transition (EMT) of pulmonary fibroblast. It is believed that if the regulation of immune response in pulmonary tissue, the inhibition of immune overreaction produced by lung, the inhibition of epithelial-mesenchymal transition (EMT) of pulmonary fibroblast and/or the inhibition of pulmonary fibroblast to myofibroblast conversion can be achieved, then the injury caused by immune reaction can be alleviated and the accumulation of the excessive amount extracellular matrix components in the pulmonary interstitial tissue can be inhibited, thus achieving the effect of delaying the onset of pulmonary fibrosis and/or treating pulmonary fibrosis.

The inventors of the present invention found that the following compound of formula (I) can effectively enhance the anti-oxidation capability of alveolar cells, and thus alleviate the oxidative stress-induced injury to the pulmonary tissue and inhibit the pulmonary fibroblast to myofibroblast conversion, inhibit the epithelial-mesenchymal transition of pulmonary fibroblasts and/or inhibit the overexpression of extracellular matrix:

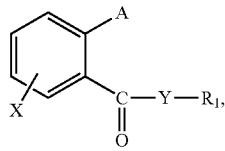

(I)

wherein, A is a C5 alkyl or alkenyl optionally substituted with —OH or =O; X is H or OH; Y is O; and $R_1$ is H or absent, with the proviso that, when $R_1$ is absent, Y and A bind together to form a five-membered ring.

The inventors of the present invention further found that for subjects treated with drugs that can induce pulmonary fibrosis, compound of formula (I) according to the present invention can effectively regulate the immune response in pulmonary tissue, alleviate the thickening of alveolar wall tissue, alleviate the abnormal infiltration of pulmonary cells and/or alleviate the decrease in pulmonary function.

Therefore, the present invention provides a medicament and a method for delaying the onset of pulmonary fibrosis and/or treating pulmonary fibrosis. The medicament comprises an active ingredient; the method comprises administrating to a subject in need an effective amount of an active ingredient. In the medicament and method according to the present invention, the active ingredient is selected from the group consisting of a compound of formula (I), a pharmaceutically acceptable salt of the compound of formula (I), and combinations thereof:

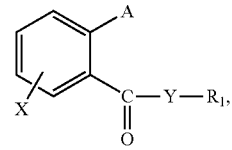

(I)

wherein, A is a C5 alkyl or alkenyl optionally substituted with —OH or =O; X is H or OH; Y is O; and $R_1$ is H or absent, with the proviso that, when $R_1$ is absent, Y and A bind together to form a five-membered ring.

In a preferred embodiment of the medicament and method according to the present invention, in the compound of formula (I), A is

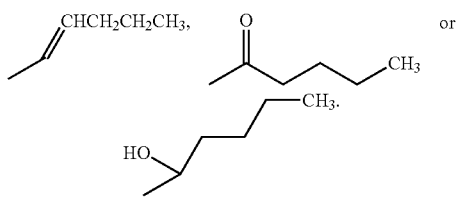

In another preferred embodiment of the medicament and method according to the present invention, in the compound of formula (I), A is

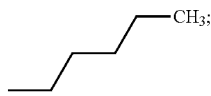

X is OH.

The particular embodiments of the compound of formula (I) according to the present invention include, but are not limited to:

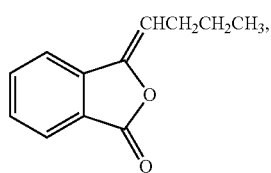

(1)

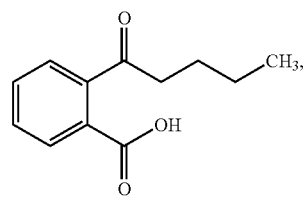

(2)

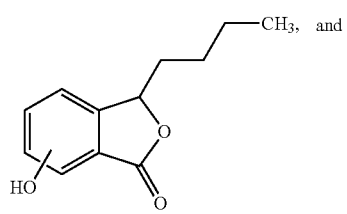

(3)

-continued

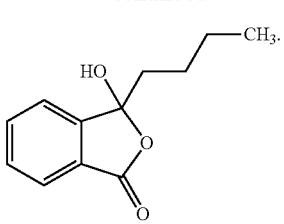

(4)

In some of the particular embodiments of the present invention, compound (1) and/or compound (2) is used to alleviate the onset of pulmonary fibrosis and/or treat pulmonary fibrosis.

As used herein, the phrase "pharmaceutically acceptable salt" includes "pharmaceutically acceptable base-addition salt" formed from "the above-mentioned compound containing functional acid group(s)" and "an organic or inorganic base," and "pharmaceutically acceptable acid-addition salt" formed from "the above-mentioned compound containing functional base group(s)" and "an organic or inorganic acid."

The examples of the "pharmaceutically acceptable base-addition salts" formed with inorganic bases include, but are not limited to, alkali metal salts (such as sodium salts and potassium salts), alkaline-earth metal salts (such as calcium salts and magnesium salts), transition metal salts (such as ferric salts, zinc salts, copper salts, manganese salts and aluminum salts) and ammonium salts.

The examples of the "pharmaceutically acceptable base-addition salts" formed with organic bases include, but are not limited to, salts formed with methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purine, piperidine, N-ethylpiperidine, tetramethylammonium compound, tetraethylammonium compound, pyridine, N,N-dimethylaniline, N-methylpiperidine, N-methylmorpholine, dicyclohexylamine, dibenzyl amine, N,N-dibenzylphenethylamine, 1-ephenamine, N,N'-benzylethylenediamine, polyamine resin, etc.

The examples of the "pharmaceutically acceptable acid-addition salts" formed with inorganic acids include, but are not limited to, salts formed with hydrobromic acid, hydrochloric acid, sulfuric acid, nitric acid, phosphoric acid, hyperchloric acid, etc.

The examples of the "pharmaceutically acceptable acid-addition salts" formed with organic acids include, but are not limited to, salts formed with sulfonic acid (such as p-toluenesulfonic acid, benzenesulfonic acid, methanesulfonic acid, ethylsulfonic acid, 2-hydroxyethanesulfonic acid and naphthalenesulfonic acid), carboxylic acid (such as acetic acid, propionic acid, fumaric acid, maleic acid, benzoic acid, salicylic acid and succinic acid), anionic amino acid (such as glutamic acid and aspartic acid), hydroxy acid (such as citric acid, lactic acid, tartaric acid, glycolic acid and malic acid), fatty acid (such as hexanoic acid, octanoic acid, decanoic acid, oleic acid and stearic acid), pamoic acid, resinolic acid, etc.

When the medicament of the present invention is used to alleviate the onset of pulmonary fibrosis and/or treat pulmonary fibrosis, depending on the desired administration manner, the medicament may be provided in any suitable form without specific limitations. For example, the medicament can be administered by an oral or parenteral (such as subcutaneous, intravenous, intramuscular, peritoneal, nasal, or transdermal) route to a subject in need, but administration is not limited thereby. A medicament in a form for oral administration is convenient for the subject to be applied by themselves. Depending on the form and purpose, suitable carriers can be chosen and used to provide the medicament, as long as the carriers do not adversely affect the desired effects of the active ingredient of the present invention, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the examples of the carrier include, but are not limited to, water, saline, dextrose, glycerol, ethanol or its analogs, cellulose, starch, sugar bentonite, and combinations thereof. The medicament can be provided in any suitable form for oral administration, such as in a solid form (such as in the form of a tablet, a pill, a capsule, granules, a pulvis), or in a liquid form (such as in the form of oral liquid, syrup, spirit, elixir, tincture), etc., but are not limited thereby.

As for the form of injection or drip suitable for subcutaneous, intravenous, intramuscular, or peritoneal administration, the medicament provided by the present invention may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the medicament as an intravenous infusion, an emulsified intravenous infusion, a powder for injection, a suspension for injection, or a powder suspension for injection, etc. Alternatively, the medicament may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administrated to a subject in need. Furthermore, as for the form of external dosage suitable for nasal or transdermal administration, the medicament can be provided in the form of, for example, liniment (such as emulsion, cream, gel, dispersing cream and ointment), spray, patch or solution (such as cleaning fluid and suspension).

As a dosage form suitable for subcutaneous implantation or interstitial implant, the medicament provided by the present invention can further comprise one or more ingredient(s) such as an excipient, stabilizer, buffer, other carrier, to prepare a medicament in a form such as a wafer, a tablet, a pill, a capsule, so that the medicament can release the active ingredient slowly and continuously to the tissue adjacent to the administration site of a subject after being administrated to the subject, and attain the effects of delaying the onset of pulmonary fibrosis and/or treating pulmonary fibrosis with a locally stable high dose of active ingredient(s). For example, but not limited to, the medicament provided by the present invention can be mixed with p(CPP-SA) copolymer to provide a mixture, and then the mixture was dissolved in dichloromethane and dried to form a powder. Then, the dried powder was filled in a mold and compressed under slight pressure to form a medicament as a wafer for subcutaneous implantation or interstitial implant.

Optionally, the medicament provided by the present invention may further comprise a suitable amount of additives, such as a flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament may optionally further comprise one or more other active ingredient(s) (such as immunomodulatory, Pirfenidone (product name: Esbriet®) and N-acetylcysteine (NAC; product name: NAC 600 mg/capsule)), or be used in combination with a medicament comprising one or more other active ingredients, to further enhance the effects of the medicament, or to increase the application flexibility and adaptability of the preparation thus provided, as long as the other active ingredients do not adversely affect the desired effects of the active ingredient of the present invention.

Depending on the need, age, body weight, and health conditions of the subject, the medicament provided by the present invention may be dosed at various administration frequencies, such as once a day, multiple times a day, or once every few days, etc. For example, when the medicament is applied orally to a subject for delaying the onset of pulmonary fibrosis and/or treating pulmonary fibrosis, the dosage of the medicament is about 1 mg (as the compound of formula (I))/kg-body weight to about 500 mg (as the compound of formula (I))/kg-body weight per day, preferably about 5 mg (as the compound of formula (I))/kg-body weight to about 200 mg (as the compound of formula (I))/kg-body weight per day, and more preferably about 10 mg (as the compound of formula (I))/kg-body weight to about 100 mg (as the compound of formula (I))/kg-body weight per day. The unit "mg/kg-body weight" refers to the dosage required per kg-body weight of the subject. However, for acute patients, the dosage may be optionally increased, for example, up to several folds or dozen folds, depending on the practical requirements. In some of the particular embodiments of the present invention, the medicament provided by the present invention is used for delaying the onset of pulmonary fibrosis and/or treating pulmonary fibrosis, wherein the dosage of the medicament is about 10 mg (as the compound of formula (I))/kg-body weight to about 50 mg (as the compound of formula (I))/kg-body weight per day.

In the method for delaying the onset of pulmonary fibrosis or treating pulmonary fibrosis according to the present invention, the applied route, applied form, suitable dosage and use of the active ingredient (i.e., the compound of formula (I), a pharmaceutically acceptable salt of the compound of formula (I), or combinations thereof) in related treatment are all in line with the above description.

The present invention will be further illustrated in detail with specific examples as follows. However, the following examples are provided only for illustrating the present invention and the scope of the present invention is not limited thereby. The scope of the present invention will be defined in the appended claims.

EXAMPLE

Experimental Material

The sources of the materials, reagents and instruments used in the Examples are as follows:

(1) Rat type II alveolar cell, L2 cell line: provided by American Type Culture Collection (ATCC), ATCC® CCL-149™;

(2) $H_2O_2$ (Hydrogen peroxide 30%): purchased from Scharlau company (Barcelona, Spain) (product number: P201405020062);

(3) N-acetylcysteine (NAC; one of the medicaments used for treating pulmonary fibrosis in clinical practice): purchased from Sigma-Aldrich company (product number: A9165);

(4) Compound (1): Lancaster Synthesis company (Newgate Morecambe, UK);

(5) Compound (2): synthesized by *Formosa* Laboratories, Inc.;

(6) 3-(4,5-Dimethylthiazol-2-yl)-2,5-diphenyltetrazolium bromide (abbreviation: MTT): purchased from Thermo Fisher company (product number: M6494);

(7) Dimethyl sulfoxide (abbreviation: DMSO): purchased from Protech company (product number: Amresco 0231);

(8) Enzyme-Linked ImmunoSorbent Assay reader (ELISA reader): Thermo Fisher company (Scientific Multiskan EX Microplate Reader);

(9) Transforming growth factor β (TGF-β): purchased from PEPROTECH Inc. (product number: 100-21);

(10) Normal Human lung fibroblasts (NHLF): purchased from Lonza company, Switzerland (product number: CC-2512);

(11) FGM-2 medium: FGM-2 SingleQuot Kit Suppl. & Growth Factors, purchased from Lonza company, Switzerland (product number: CC-4126);

(12) Pirfenidone (one of the medicaments used for treating pulmonary fibrosis in the clinical practice): purchased from Sigma-Aldrich company (product number: P2116);

(13) C57B/L6 mice: purchased from the National Laboratory Animal Center;

(14) Bleomycin sulfate (inducer of pulmonary fibrosis): purchased from Sigma-Aldrich company (product number: B5507);

(15) Olive oil: Olitalia extra virgin food grade olive oil;

(16) Unrestrained Whole Body Plethysmography (WBP): purchased from Buxco company;

(17) PRO-PREP™ Protein Extraction Kit: purchased from iNtRON company;

(18) RNeasy Mini Kit: purchased form Qiagen company;

(19) QuantiTect Reverse Transcription Kit: purchased form Qiagen company;

(20) Fugene HD transfection reagent: purchased form Promega company; and

(21) SOX2 gene plasmid (pcDNA3.1-SOX2): synthesized by GENEWIZ company (Accession No.: NM_003106.3).

In Vitro Experiment

Example 1: Cell Survival Test (MTT Analysis)

It is known that oxidative stress can cause the death of alveolar cells, and make injury to pulmonary tissue. An in vitro experiment is used to ascertain whether the compound of formula (I) of the present invention can alleviate the oxidative stress-induced injury to the pulmonary tissue.

The rat type II alveolar cell, L2 cell line (ATCC® CCL149™) were seeded into a 96-well plate at a density of $5 \times 10^3$ cells/well, 48 wells in total (separated into a control group and five experimental groups, 8 wells for each group). The cells were cultured until the next day, and then the mediums were removed. Each group was respectively treated under the following conditions to conduct follow-up experiments:

(1) Control group: cells were cultured in a F-12K medium (Kaighn's Modification of Ham's F-12 Medium, ATCC® 30-2004™) for 24 hours;

(2) Group 1: cells were cultured in a F-12K medium containing $H_2O_2$ (0.1 mM) for 24 hours;

(3) Group 2: cells were cultured in a F-12K medium containing $H_2O_2$ (0.1 mM) and compound (1) (5 μg/ml) for 24 hours;

(4) Group 3: cells were cultured in a F-12K medium containing $H_2O_2$ (0.1 mM) and N-acetylcysteine (NAC) (2 mM) for 24 hours;

(5) Group 4: cells were cultured in a F-12K medium containing $H_2O_2$ (0.2 mM) and compound (1) (5 μg/ml) for 24 hours; and (6) Group 5: cells were cultured in a F-12K medium containing $H_2O_2$ (0.2 mM) and NAC (2 mM) for 24 hours.

The mediums were removed after culturing was complete, and then each group was respectively treated under the following conditions: F-12K mediums containing 10% of 3-(4,5-Dimethylthiazol-2-yl)-2,5-diphenyltetrazolium bromide (MTT) were added into each well, and cultured for 1 hour. Thereafter, the mediums were removed, and a suitable amount of dimethyl sulfoxide (DMSO) was added into the wells. An Enzyme-Linked ImmunoSorbent Assay reader (ELISA reader) was then used for detecting the absorbance of each group at a wavelength of 595 nm ($OD_{595nm}$). The average value of each group was respectively calculated (n=8), and then the result of the control group served as the basis for calculating the relative survival rates of the other groups. The results are shown in FIG. 1 and Table 1.

TABLE 1

| | Group | | | | | |
|---|---|---|---|---|---|---|
| | Control group | Group 1 | Group 2 | Group 3 | Group 4 | Group 5 |
| Relative survival rate | 100% | 38.9% | 109.4% | 101.9% | 80.6% | 83.1% |

As shown in FIG. 1 and Table 1, as compared to the control group, the survival rate of group 1 significantly decreased. However, as compared to group 1, the survival rates of groups 2, 3, 4 and 5 all significantly increased. The above results show that $H_2O_2$ can produce oxidative stress to lung tissue, resulting in the death of alveolar cells. The compound of formula (I) of the present invention has the effects of enhancing the anti-oxidation capability of alveolar cells, increasing the survival rate of alveolar cells, and alleviating the oxidative stress-induced injury to the pulmonary tissue, and those effects are comparable to that of the medicaments used for treating pulmonary fibrosis in clinical practice.

Example 2: Effects of the Compound of Formula (I) on Inhibiting the Expression of Collagen When immune overreaction occurs in the lungs, the TGF-β signaling pathway is activated, and further leads to injury to pulmonary tissue. Pulmonary fibroblasts will then secrete extracellular matrix components such as collagen, elastin and fibronectin to repair the tissue. However, the overreaction of tissue repairing (i.e., by secreting an excessive amount of extracellular matrix components) will cause pulmonary fibrosis. BMP-7 can inhibit the activation of the TGF-β signaling pathway. The following experiments (2-1) and (2-2) were conducted to ascertain whether the compound of formula (I) of the present invention has the ability to inhibit pulmonary fibroblasts from overly secreting extracellular matrix components (such as collagen).

(2-1)
Normal Human lung fibroblasts (NHLF) were seeded into 6 cm culture dishes at a density of $2\times10^5$ cells/dish, comprising a control group and three experimental groups (4 dishes in total). The cells were cultured until the next day, and then the mediums were removed. Each group was respectively treated under the following conditions to conduct follow-up experiments:

(1) Positive control group: cells were cultured in a FGM-2 medium containing 1% serum for 36 hours;

(2) Negative control group: cells were cultured in a FGM-2 medium containing 1% serum and TGF-β1 (5 ng/ml) for 36 hours;

(3) Low-dose group: cells were firstly cultured in a FGM-2 medium containing 1% serum and TGF-β1 (5 ng/ml) for 12 hours, and then compound (1) was added into the medium to provide a final concentration of 15 μg/ml; thereafter, the cells were cultured for another 24 hours; and (4) High-dose group: cells were firstly cultured in a FGM-2 medium containing 1% serum and TGF-β1 (5 ng/ml) for 12 hours, and then compound (1) was added into the medium to provide a final concentration of 25 μg/ml; thereafter, the cells were cultured for another 24 hours.

Thereafter, the proteins in the cells of each group were extracted, and the expressions of type I collagen in the NHLF cells of each group were measured with western blotting, wherein the β-actin served as the internal control. The results of the control group served as the basis for calculating the relative expression levels of the other groups. The results are shown in FIG. 2 and Table 2.

TABLE 2

| Group | Positive control group | Negative control group | Low-dose group | High-dose group |
|---|---|---|---|---|
| Relative expression level of the type I collagen (fold) | 1 | 3.61 | 3.56 | 1.83 |

Figure 2:
FIG. 2 is a photograph showing the expressions of type I collagen and β-actin in normal human lung fibroblasts (NHLFs) cultured with different conditions, wherein the expression results were analyzed by western blotting, the positive control group was not induced by TGF-β1 and was cultured in a medium that was free of compound (1), the negative control group was induced by TGF-β1 and cultured in a medium that was free of compound (1), the low-dose group was induced by TGF-β1 and cultured in a medium containing a low concentration of compound (1) (15 μg/ml), and the high-dose group was induced by TGF-β1 and cultured in a medium containing a high concentration of compound (1) (25 μg/ml)

As shown in FIG. 2 and Table 2, as compared to the positive control group, the expression level of collagen in the negative control group induced by TGF-β1 significantly increased. However, as compared to the negative control group, the expression level of collagen in the low-dose group decreased a little, while the expression level of collagen in the high-dose group decreased significantly.

The above results show that TGF-β1 can induce pulmonary fibroblasts to express a large amount of collagen, while the compound of formula (I) of the present invention has the effect on inhibiting the overexpression of collagen, wherein the effect increased along with the increasing concentration of the compound of formula (I).

(2-2)
Normal Human lung fibroblasts (NHLF) were seeded into 6 cm culture dishes at a density of $2\times10^5$ cells/dish, comprising a control group and six experimental groups (7 dishes in total). The cells were cultured until the next day, and then the mediums were removed. Each group was respectively treated under the following conditions to conduct follow-up experiments:

(1) Positive control group: cells were cultured in a FGM-2 medium containing 1% serum and TGF-β1 (5 ng/ml) for 36 hours;

(2) Group I: cells were firstly cultured in a FGM-2 medium containing 1% serum and TGF-β1 (5 ng/ml) for 12 hours, and then compound (1) was added into the medium to provide a final concentration of 15 μg/ml; thereafter, the cells were cultured for another 24 hours;

(3) Group II: cells were firstly cultured in a FGM-2 medium containing 1% serum and TGF-β1 (5 ng/ml) for 12 hours, and then compound (1) was added into the medium to provide a final concentration of 25 μg/ml; thereafter, the cells were cultured for another 24 hours;

(4) Group III: cells were firstly cultured in a FGM-2 medium containing 1% serum and TGF-β1 (5 ng/ml) for 12 hours, and then compound (1) was added into the medium to provide a final concentration of 35 μg/ml; thereafter, the cells were cultured for another 24 hours;

(5) Group IV: cells were firstly cultured in a FGM-2 medium containing 1% serum and TGF-β1 (5 ng/ml) for 12 hours, and then the Pirfenidone was added into the medium to provide a final concentration of 100 μg/ml; thereafter, the cells were cultured for another 24 hours;

(6) Group V: cells were firstly cultured in a FGM-2 medium containing 1% serum and TGF-β1 (5 ng/ml) for 12 hours, and then the Pirfenidone was added into the medium to provide a final concentration of 250 μg/ml; thereafter, the cells were cultured for another 24 hours; and (7) Group VI: cells were firstly cultured in a FGM-2 medium containing 1% serum and TGF-β1 (5 ng/ml) for 12 hours, and then the Pirfenidone was added into the medium to provide a final concentration of 500 μg/ml; thereafter, the cells were cultured for another 24 hours.

Thereafter, the proteins in the cells of each group were extracted, and the expressions of type I collagen, BMP-7 protein and TGF-β protein in the NHLF cells of each group were measured with western blotting. The results of the control group served as the basis for calculating the relative expression levels of the other groups. The results are shown in FIG. 3 and Table 3.

TABLE 3

| Group | Relative expression level (fold) | | |
|---|---|---|---|
| | Type I collagen | BMP-7 protein | TGF-β protein |
| Control group | 1 | 1 | 1 |
| Group I | 0.79 | 1.57 | 0.81 |
| Group II | 0.30 | 1.80 | 0.77 |
| Group III | 0.51 | 1.68 | 0.58 |
| Group IV | 0.95 | 1.52 | 0.67 |
| Group V | 0.57 | 1.43 | 0.64 |
| Group VI | 0.50 | 1.34 | 0.67 |

Figure 3:
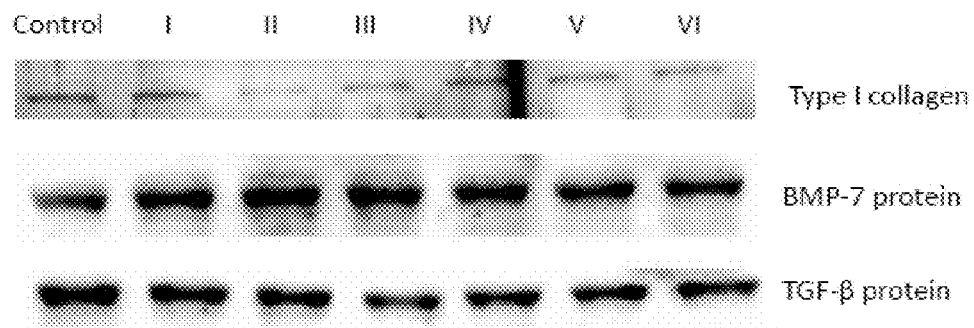
FIG. 3 is a photograph showing the expressions of type I collagen, BMP-7 protein and TGF-β protein in normal human lung fibroblasts (NHLFs) induced by TGF-β1 and cultured in different mediums, wherein the expression results were analyzed by western blotting, the control group was cultured in a FGM-2 medium, group I was cultured in a FGM-2 medium containing compound (1) (15 μg/ml), group II was cultured in a FGM-2 medium containing compound (1) (25 μg/ml), group III was cultured in a FGM-2 medium containing compound (1) (35 μg/ml), group IV was cultured in a FGM-2 medium containing Pirfenidone (100 μg/ml), group V was cultured in a FGM-2 medium containing Pirfenidone (250 μg/ml), and group VI was cultured in a FGM-2 medium containing Pirfenidone (500 μg/ml)

As shown in FIG. 3 and Table 3, as compared to the control group, the expression levels of collagen and TGF-β protein in groups I, II, III, IV, V, and VI all significantly decreased. In another aspect, as compared to the control group, the expression levels of BMP-7 protein in groups I, II, III, IV, V, and VI all significantly increased.

The above results show that the compound of formula (I) of the present invention can increase the level of BMP-7 protein expressed by the pulmonary fibroblasts, and inhibit the overexpression of collagen induced by TGF-β1, wherein the effect increased along with the increasing concentration of the compound of formula (I). This illustrates that the compound of formula (I) of the present invention can inhibit the TGF-β signaling pathway by increasing the expression of BMP-7, and thus has the effect on inhibiting the overexpression of collagen. The effect of the compound of formula (I) is better than that of medicaments used for treating pulmonary fibrosis in the present clinical practice.

(2-3)

The pcDNA3.1 empty vector and the pcDNA3.1-SOX2 plasmid (i.e., pcDNA3.1 vector containing SOX2 gene) were respectively transfected into Normal Human lung fibroblasts (NHLF) by the Fugene HD cell transfection reagent. The cells were screened to obtain NHLFs containing the pcDNA3.1 empty vector or the pcDNA3.1-SOX2 plasmid.

NHLFs containing the pcDNA3.1 empty vector were then seeded into 6 cm culture dishes at a density of $2 \times 10^5$ cells/dish, comprising a control group and three experimental groups (4 dishes in total). The cells were cultured until the next day, and then the mediums were removed. Each group was respectively treated under the following conditions to conduct follow-up experiments:

(1) Control group I: cells were cultured in a FGM-2 medium containing 1% serum for 36 hours;

(2) Group A: cells were cultured in a FGM-2 medium containing 1% serum and TGF-β1 (5 ng/ml) for 36 hours;

(3) Group B: cells were firstly cultured in a FGM-2 medium containing 1% serum and TGF-β1 (5 ng/ml) for 12 hours, and then compound (1) was added into the medium to provide a final concentration of 15 μg/ml; thereafter, the cells were cultured for another 24 hours; and (4) Group C: cells were firstly cultured in a FGM-2 medium containing 1% serum and TGF-β1 (5 ng/ml) for 12 hours, and then compound (1) was added into the medium to provide a final concentration of 30 μg/ml; thereafter, the cells were cultured for another 24 hours.

In another aspect, NHLFs containing the pcDNA3.1-SOX2 plasmid were seeded into the 6 cm culture dishes at a density of $2 \times 10^5$ cells/dish, comprising a control group and three experimental groups (4 dishes in total). The cells were cultured until the next day, and then the mediums were removed. Each group was respectively treated under the following conditions to conduct follow-up experiments:

(1) Control group II: cells were cultured in a FGM-2 medium containing 1% serum for 36 hours;

(2) Group D: cells were cultured in a FGM-2 medium containing 1% serum and TGF-β1 (5 ng/ml) for 36 hours;

(3) Group E: cells were firstly cultured in a FGM-2 medium containing 1% serum and TGF-β1 (5 ng/ml) for 12 hours, and then the compound (1) was added into the medium to provide a final concentration of 15 μg/ml; thereafter, the cells were cultured for another 24 hours; and (4) Group F: cells were firstly cultured in a FGM-2 medium containing 1% serum and TGF-β1 (5 ng/ml) for 12 hours, and then the compound (1) was added into the medium to provide a final concentration of 30 μg/ml; thereafter, the cells were cultured for another 24 hours.

Thereafter, the proteins in the cells of each group were extracted, and the expressions of Sox2 protein, TGF-β protein and type I collagen in the NHLF cells of each group were measured with western blotting. The results of the control group served as the basis for calculating the relative expression levels of the other groups. The results are shown in FIG. 4 and Table 4.

TABLE 4

| | | Relative expression level (fold) | | |
|---|---|---|---|---|
| | Group | Sox2 protein | TGF-β protein | Type I collagen |
| pcDNA3.1 empty vector | Control group I | 1 | 1 | 1 |
| | Group A | 1.55 | 0.84 | 5.83 |
| | Group B | 1.81 | 0.89 | 3.74 |
| | Group C | 1.04 | 0.69 | 0.88 |
| pcDNA3.1-SOX2 plasmid | Control group II | 1 | 1 | 1 |
| | Group D | 0.88 | 0.86 | 1.57 |
| | Group E | 1.03 | 0.83 | 1.30 |
| | Group F | 1.02 | 0.71 | 1.29 |

Figure 4:
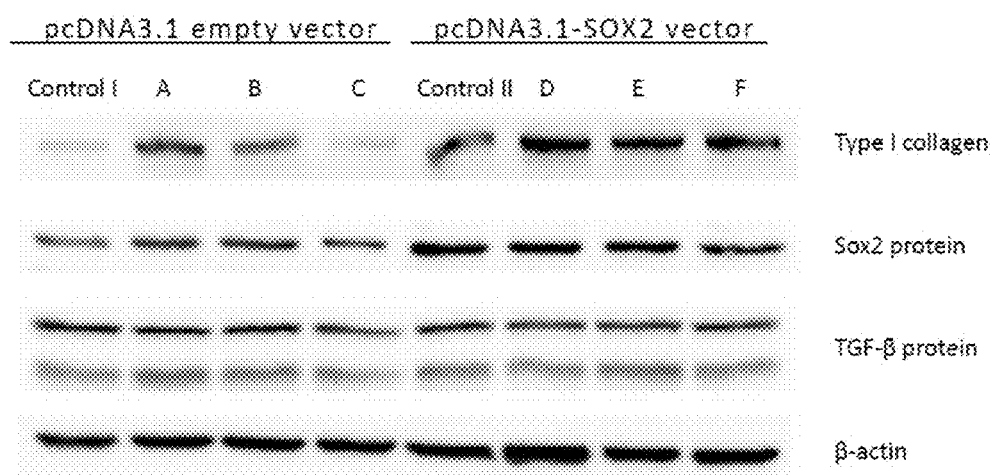
FIG. 4 is a photograph showing the expressions of Sox2 protein, TGF-β protein, and type I collagen protein in normal human lung fibroblasts (NHLFs) containing pcDNA3.1 empty vectors (control group I and groups A to C) or pcDNA3.1-SOX 2 plasmids (control group II and groups D to F) after cultured in different mediums, wherein the expression results were analyzed by western blotting, control group I and control group II were not induced by TGF-β1 and were cultured in a medium that was free of compound (1), group A and group D were induced by TGF-β1 and were cultured in a medium that was free of compound (1), group B and group E were induced by TGF-β1 and were cultured in a medium containing 15 μg/ml compound (1), group C and group F were induced by TGF-β1 and were cultured in a medium containing 30 μg/ml compound (1)

As shown in FIG. 4, as compared to the NHLFs containing the pcDNA3.1 empty vector (the control group I and groups A to C), the expression level of Sox2 protein in the NHLFs containing the pcDNA3.1-SOX2 plasmid (the control group II and groups D to F) was significantly higher, which shows that the pcDNA3.1-SOX2 plasmid had already been transfected into the NHLFs in the above transfection experiment.

In another aspect, as shown in FIG. 4 and Table 4, as compared to group A, the expression levels of Sox2 protein, TGF-β protein and type I collagen in group C all significantly decreased. As compared to group D, the expression levels of TGF-β protein and type I collagen in groups E and F did not significantly decrease. The above results show that the compound of formula (I) of the present invention can inhibit the expressions of TGF-β protein and type I collagen in pulmonary fibroblasts, but when Sox2 protein was overexpressed, the compound of formula (I) did not inhibit the expressions of TGF-β protein and type I collagen. This illustrates that the compound of formula (I) can inhibit the expressions of TGF-β protein and type I collagen by regulating Sox2 protein, and thus alleviates pulmonary fibrosis.

Example 3: Effect of the Compound of Formula (I) on Inhibiting Pulmonary Fibroblast to Myofibroblast Conversion It is known that the activation of the TGF-β signaling pathway can stimulate pulmonary fibroblasts to proliferate and convert into myofibroblast, while BMP-7 can inhibit the activation of the TGF-β signaling pathway. A myofibroblast is a kind of cell that expresses the α-SMA marker protein and has a high migration ability. When the myofibroblast is activated, it will secrete an excessive amount of extracellular matrix components, which accumulate in the pulmonary interstitial tissue and then form the microenvironment for pulmonary fibrosis. Therefore, the following experiments (3-1) and (3-2) were conducted to ascertain whether the compound of formula (I) of the present invention has the ability to inhibit pulmonary fibroblast to myofibroblast conversion.

(3-1)

Normal Human lung fibroblasts (NHLF) were seeded into 6 cm culture dishes at a density of 2×10⁵ cells/dish, comprising a control group and six experimental groups (7 dishes in total). The cells were cultured until the next day, and then the mediums were removed. Each group was respectively treated under the following conditions to conduct follow-up experiments:

(1) Control group: cells were cultured in a FGM-2 medium containing 10% serum for 36 hours;
(2) Group i: cells were cultured in a FGM-2 medium containing 1% serum for 36 hours;
(3) Group ii: cells were firstly cultured in a FGM-2 medium containing 1% serum for 12 hours, and then compound (1) was added into the medium to provide a final concentration of 15 μg/ml; thereafter, the cells were cultured for another 24 hours;
(4) Group iii: cells were firstly cultured in a FGM-2 medium containing 1% serum for 12 hours, and then compound (1) was added into the medium to provide a final concentration of 25 μg/ml; thereafter, the cells were cultured for another 24 hours;
(5) Group iv: cells were cultured in a FGM-2 medium containing 1% serum and TGF-β1 (5 ng/ml) for 36 hours;
(6) Group v: cells were firstly cultured in a FGM-2 medium containing 1% serum and TGF-β1 (5 ng/ml) for 12 hours, and then compound (1) was added into the medium to provide a final concentration of 15 μg/ml; thereafter, the cells were cultured for another 24 hours; and
(7) Group vi: cells were firstly cultured in a FGM-2 medium containing 1% serum and TGF-β1 (5 ng/ml) for 12 hours, and then compound (1) was added into the medium to provide a final concentration of 25 μg/ml; thereafter, the cells were cultured for another 24 hours.

Thereafter, the proteins in the cells of each group were extracted, and the expressions of BMP-7 protein, TGF-β protein and α-SMA protein in the NHLF cells of each group were measured with western blotting, wherein the β-actin served as the internal control. The results of the control group served as the basis for calculating the relative expression levels of the other groups. The results are shown in FIG. 5 and Table 5.

TABLE 5

| | Relative expression level (fold) | | |
|---|---|---|---|
| Group | BMP-7 protein | TGF-β protein | α-SMA protein |
| Control group | 1 | 1 | 1 |
| Group i | 1 | 0.66 | 0.94 |
| Group ii | 0.91 | 0.63 | 0.95 |
| Group iii | 0.81 | 0.52 | 0.89 |
| Group iv | 0.82 | 0.80 | 0.89 |
| Group v | 0.76 | 0.79 | 0.72 |
| Group vi | 1.07 | 0.59 | 0.77 |

Figure 5:
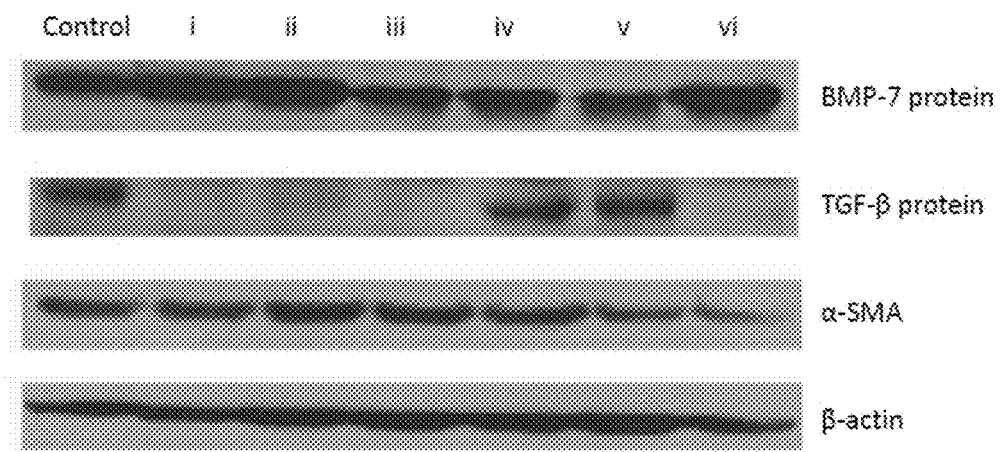
FIG. 5 is a photograph showing the expressions of BMP-7 protein, TGF-β protein, and α-SMA protein in the normal human lung fibroblasts (NHLFs) cultured in different mediums, wherein the expression results were analyzed by western blotting, the control group was cultured in a FGM-2 medium containing 10% serum, group i was cultured in a FGM-2 medium containing 1% serum, group ii was cultured in a FGM-2 medium containing 1% serum and compound (1) (15 μg/ml), group iii was cultured in a FGM-2 medium containing 1% serum and compound (1) (25 μg/ml), group iv was cultured in a FGM-2 medium containing 1% serum and TGF-β1 (5 ng/ml), group v was cultured in a FGM-2 medium containing 1% serum, TGF-β1 (5 ng/ml), and compound (1) (15 μg/ml), and group vi was cultured in a FGM-2 medium containing 1% serum, TGF-β1 (5 ng/ml), and compound (1) (25 μg/ml)

As shown in FIG. 5 and Table 5, as compared to group iv, the expression levels of TGF-β protein and α-SMA protein in groups v and vi all decreased.

The above results show that the compound of formula (I) can inhibit the activation of the TGF-β signaling pathway in pulmonary fibroblasts, and inhibit the expression of the marker proteins of myofibroblast. This illustrates that the compound of formula (I) has the effect on inhibiting pulmonary fibroblast to myofibroblast conversion.

(3-2)

Normal Human lung fibroblasts (NHLF) were seeded into 6-well plate at a density of 10⁵ cells/well, comprising a control group and five experimental groups (6 wells in total). The cells were cultured until the next day, and then the mediums were removed. Each group was respectively treated under the following conditions to conduct follow-up experiments:

(1) Control group: cells were cultured in a FGM-2 medium containing 1% serum for 24 hours;
(2) Group α: cells were cultured in a FGM-2 medium containing 1% serum and compound (1) (5 μg/ml) for 24 hours;

(3) Group β: cells were cultured in a FGM-2 medium containing 1% serum and compound (1) (10 μg/ml) for 24 hours;
(4) Group γ: cells were cultured in a F-12K medium containing 1% serum and $H_2O_2$ (0.1 mM) for 24 hours;
(5) Group δ: cells were cultured in a F-12K medium containing 1% serum, $H_2O_2$ (0.1 mM) and compound (1) (5 μg/ml) for 24 hours; and
(6) Group ε: cells were cultured in a F-12K medium containing 1% serum, $H_2O_2$ (0.1 mM) and compound (1) (10 μg/ml) for 24 hours.

Thereafter, the total RNA of cells taken from each group were extracted, and then reverse transcription was conducted on the total RNA by using a QuantiTect Reverse Transcription Kit to obtain cDNA therefrom. A Q-PCR was then conducted on the cDNA to analyze the mRNA expression levels of genes such as α-SMA and TGF-β, wherein GAPDH gene served as an internal control. The results of the control group served as the basis for calculating the relative expression levels of the other groups. The results are shown in FIG. 6 and Table 6.

TABLE 6

| Group | Relative expression level (fold) | |
|---|---|---|
| | α-SMA | TGF-β |
| Control group | 1 | 1 |
| Group α | 0.46 | 0.61 |
| Group β | 0.64 | 0.12 |
| Group γ | 0.92 | 0.34 |
| Group δ | 0.56 | 0.42 |
| Group ε | 0.37 | 0.04 |

Figure 6:
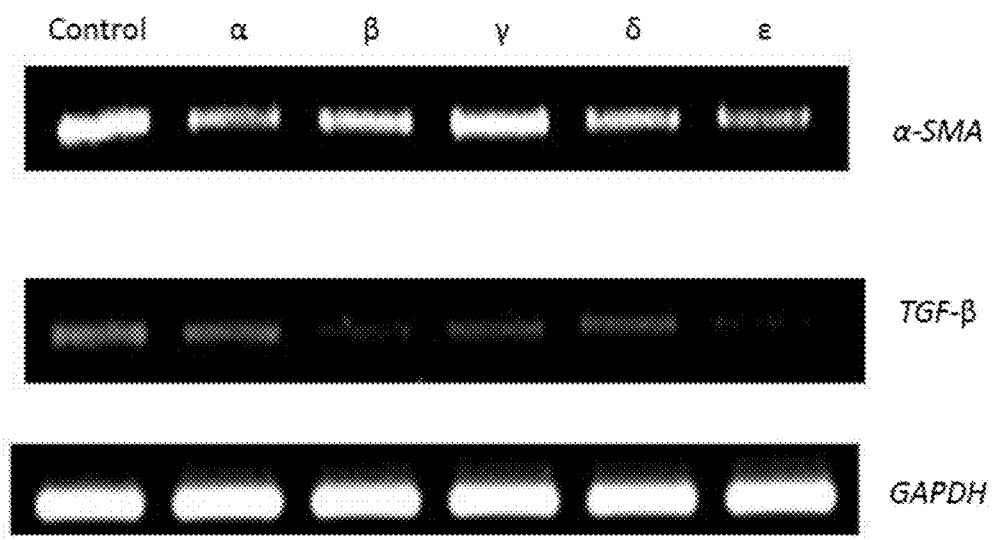
FIG. 6 is a photograph showing the gene expressions of α-SMA and TGF-β in normal human lung fibroblasts (NHLFs) cultured in different mediums, wherein the expression results were analyzed by RT-PCR, the control group was cultured in a FGM-2 medium, group α was cultured in a FGM-2 medium containing compound (1) (5 μg/ml), group β was cultured in a FGM-2 medium containing compound (1) (10 μg/ml), group γ was cultured in a F-12K medium containing $H_2O_2$ (0.1 mM), group δ was cultured in a F-12K medium containing $H_2O_2$ (0.1 mM) and compound (1) (5 μg/ml), and group ε was cultured in a F-12K medium containing $H_2O_2$ (0.1 mM) and compound (1) (10 μg/ml)

As shown in FIG. 6 and Table 6, as compared to the control group, the mRNA expressions of α-SMA and TGF-β genes in each experimental group (i.e., groups α, β, γ, δ and ε) all decreased.

The above results show that even when the cells are under oxidative stress produced by $H_2O_2$, the compound of formula (I) of the present invention can still inhibit the expressions of α-SMA and TGF-β genes resulting from pulmonary fibroblasts. This illustrates that the compound of formula (I) can inhibit the activation of the TGF-β signaling pathway in pulmonary fibroblasts, and inhibit the expression of the marker proteins in myofibroblasts.

The results of the above experiments (3-1) and (3-2) show that the compound of formula (I) of the present invention can inhibit pulmonary fibroblast to myofibroblast conversion, and thus the compound of formula (I) has the effect of preventing the accumulation of an excessive amount of extracellular matrix components (such as collagen, elastin and fibronectin) in pulmonary interstitial tissue.

Example 4: Effect of the Compound of Formula (I) on Inhibiting the Epithelial-Mesenchymal Transition (EMT) of Pulmonary Fibroblasts It is known that the activation of the TGF-β/Smad signaling pathway will promotes the epithelial-mesenchymal transition, and BMP-7 can inhibit the activation of the TGF-β/Smad signaling pathway. When the cells perform the epithelial-mesenchymal transition, the polarity between the cells decreases gradually and the migration ability of the cells increases, and thus the cells are more easily to creep and invade, leading to the cells being further involved in the fibrosis of tissue. Therefore, the following experiment was conducted to ascertain whether the compound of formula (I) of the present invention has the ability to inhibit the epithelial-mesenchymal transition of pulmonary fibroblasts.

Normal Human lung fibroblasts (NHLF) were seeded into 6 cm culture dishes at a density of $2\times10^5$ cells/dish, comprising a control group and five experimental groups (6 dishes in total). The cells were cultured until the next day, and then the mediums were removed. Each group was respectively treated under the following conditions to conduct follow-up experiments:
(1) Control group: cells were cultured in a FGM-2 medium containing 1% serum for 36 hours;
(2) Group A: cells were cultured in a FGM-2 medium containing 1% serum and TGF-β1 (5 ng/ml) for 36 hours;
(3) Group B: cells were firstly cultured in a FGM-2 medium containing 1% serum and TGF-β1 (5 ng/ml) for 12 hours, and then compound (1) was added into the medium to provide a final concentration of 15 μg/ml; thereafter, the cells were cultured for another 24 hours;
(4) Group C: cells were firstly cultured in a FGM-2 medium containing 1% serum and TGF-β1 (5 ng/ml) for 12 hours, and then compound (1) was added into the medium to provide a final concentration of 30 μg/ml; thereafter, the cells were cultured for another 24 hours;
(5) Group D: cells were firstly cultured in a FGM-2 medium containing 1% serum and TGF-β1 (5 ng/ml) for 12 hours, and then compound (2) was added into the medium to provide a final concentration of 100 μg/ml; thereafter, the cells were cultured for another 24 hours; and
(6) Group E: cells were firstly cultured in a FGM-2 medium containing 1% serum and TGF-β1 (5 ng/ml) for 12 hours, and then compound (2) was added into the medium to provide a final concentration of 200 μg/ml; thereafter, the cells were cultured for another 24 hours.

Thereafter, the proteins in the cells of each group were extracted, and the expressions of BMP-7 protein, TGF-β protein and p-smad2/3 protein in the NHLF cells of each group were measured with western blotting. The results of the control group served as the basis for calculating the relative expression levels of the other groups. The results are shown in FIG. 7 and Table 7.

TABLE 7

| Group | Relative expression level (fold) | | |
|---|---|---|---|
| | BMP-7 protein | TGF-β protein | p-smad2/3 protein |
| Control group | 1 | 1 | 1 |
| Group A | 0.19 | 1.75 | 1.42 |
| Group B | 0.68 | 1.27 | 0.82 |
| Group C | 0.31 | 1.34 | 1.08 |
| Group D | 0.11 | 0.46 | 1.12 |
| Group E | 0.08 | 0.29 | 1.05 |

Figure 7:
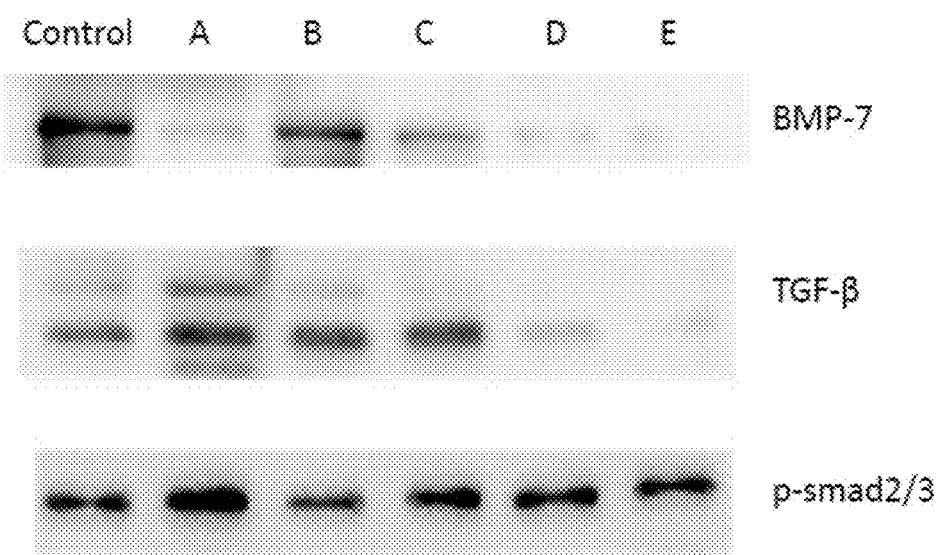
FIG. 7 is a photograph showing the expressions of BMP-7 protein, TGF-β protein, and p-smad2/3 protein in normal human lung fibroblasts (NHLFs) cultured with different conditions, wherein the expression results were analyzed by western blotting, the control group was not induced by TGF-β1 and was cultured in a medium that was free of compound (1) or compound (2), group A was induced by TGF-β1 and cultured in a medium that was free of compound (1) or compound (2), group B was induced by TGF-β1 and cultured in a medium containing 15 μg/ml compound (1), group C was induced by TGF-β1 and cultured in a medium containing 30 μg/ml compound (1), group D was induced by TGF-β1 and cultured in a medium containing 100 μg/ml compound (2), and group E was induced by TGF-β1 and cultured in a medium containing 200 μg/ml compound (2)
Figure 8A:
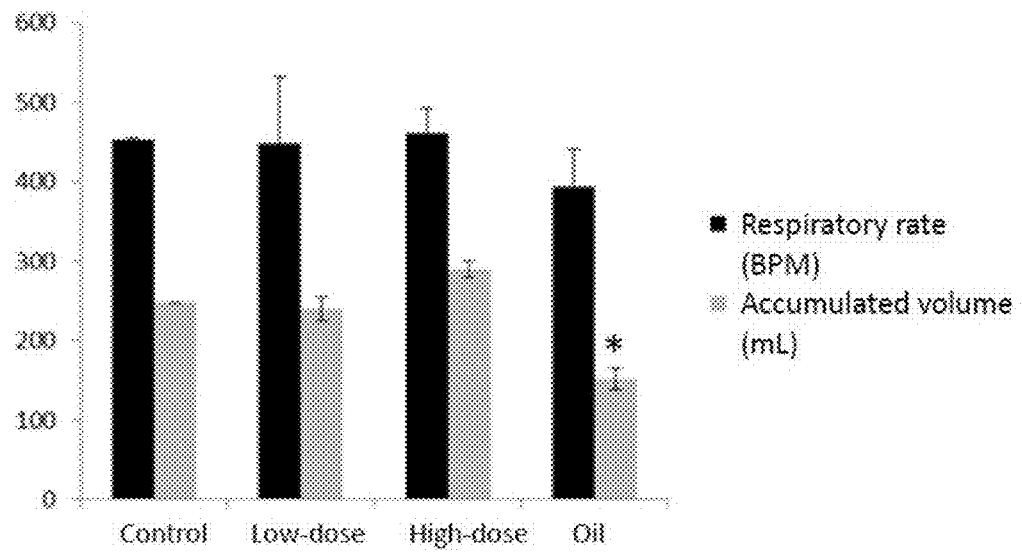
FIGS. 8A to 8D show the pulmonary functions of mice treated with different conditions, wherein the results were evaluated by an unrestrained whole body plethysmography (WBP)
Figure 8B:
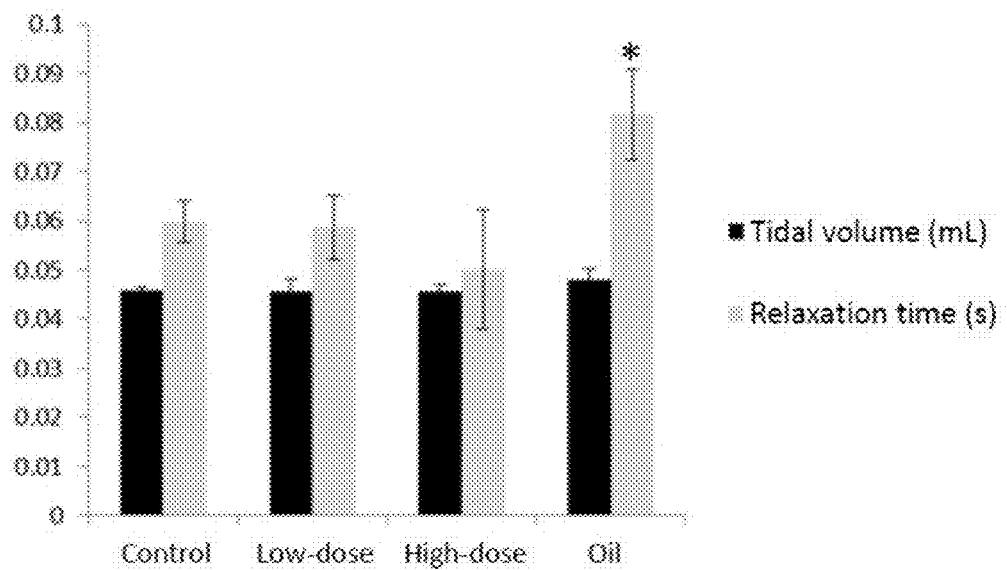
Figure 8C:
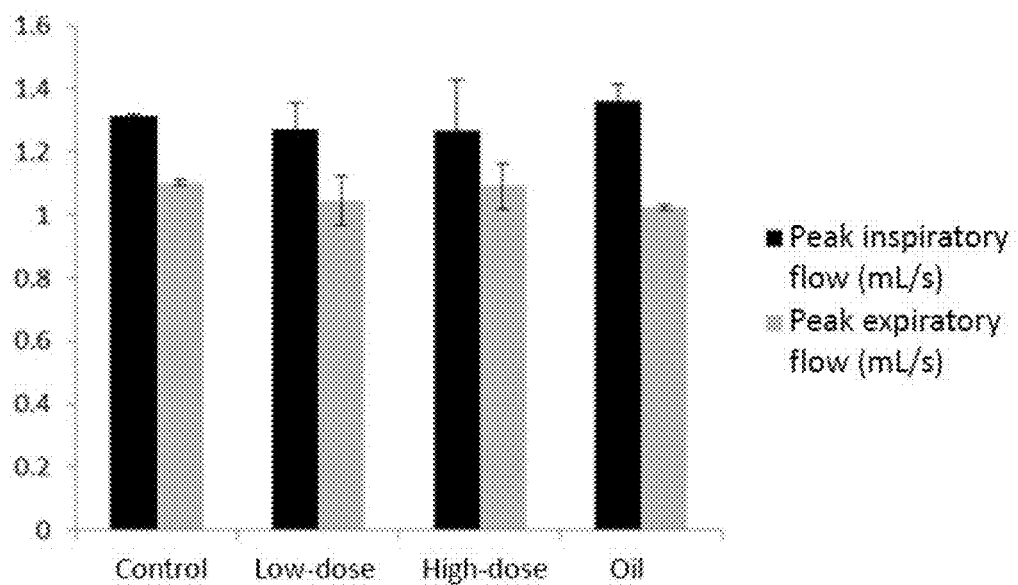
Figure 8D:
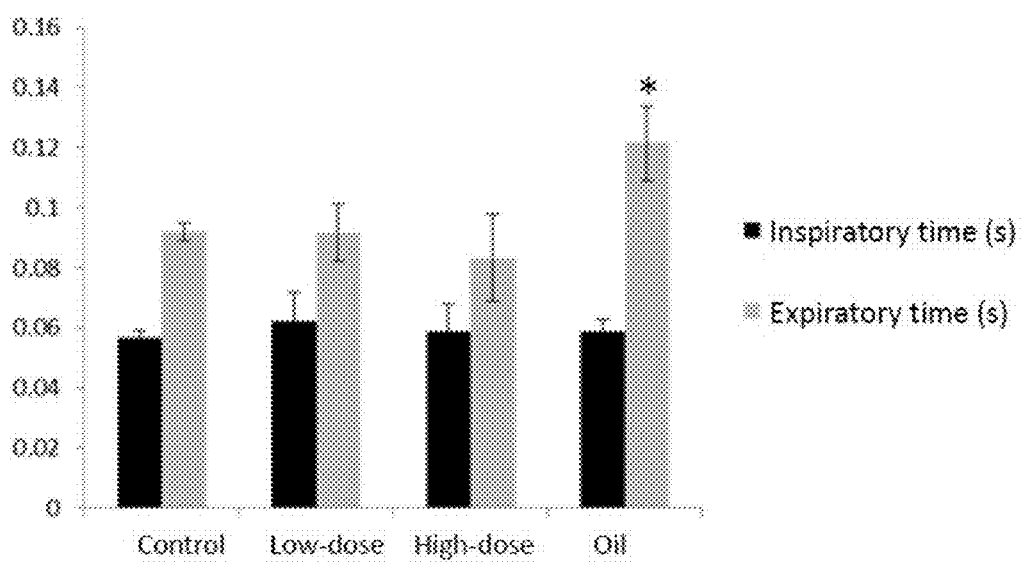

As shown in FIG. 7 and Table 7, as compared to group A, the expression levels of BMP-7 protein in groups B and C were significantly higher, and the expression levels of TGF-β protein and p-smad2/3 protein in groups B and C were significantly lower. Besides, as compared to group A, the expression levels of TGF-β protein and p-smad2/3 protein in groups D and E were also significantly lower.

The above results show that the compound of formula (I) of the present invention can inhibit the expression of TGF-β protein in pulmonary fibroblasts, and inhibit the phosphorylation of smad2 and smad3 proteins. This illustrates that the compound of formula (I) can inhibit the activation of the TGF-β/Smad signaling pathway, and thus the compound of formula (I) has the effect on inhibiting the epithelial-mesenchymal transition of the pulmonary fibroblast.

In Vivo Experiment

Example 5: Establishment of the Animal Model

24 C57B/L6 mice (age: four weeks) were separated into four groups (6 mice in each group). Each group was respectively treated under the following conditions to conduct follow-up experiments:
(1) Control group (mice without pulmonary fibrosis; i.e., normal mice): 50 µl of PBS was administered to each mouse by intratracheal injection, and then the mice were fed for 30 days;
(2) Oil group: 0.6 U/50 µl of Bleomycin sulfate (dissolved in PBS) was administered to each mouse by intratracheal injection, and then 100 µl of olive oil was orally administered to each mouse every day for 30 days;
(3) Low-dose group: 0.6 U/50 µl of Bleomycin sulfate (dissolved in PBS) was administered to each mouse by intratracheal injection, and then compound (1) (10 mg/kg-body weight, prepared with olive oil to provide a final volume of 100 µl) was orally administered to each mouse every day for 30 days; and
(4) High-dose group: 0.6 U/50 µl of Bleomycin sulfate (dissolved in PBS) was administered to each mouse by intratracheal injection, and then compound (1) (50 mg/kg-body weight, prepared with olive oil to provide a final volume of 100 µl) was orally administered to each mouse every day for 30 days.

Example 6: Measurement of Pulmonary Function

When definitely diagnosed, most of the pulmonary fibrosis patients' pulmonary functions had already decreased, and those patients also had the symptom of dyspnea. Patients with late-stage pulmonary fibrosis further exhibited heart failure, respiratory failure, etc. caused by long term hypoxia. Therefore, the following experiment was conducted to ascertain whether the compound of formula (I) of the present invention can maintain pulmonary function and alleviate the decrease in pulmonary function.

In this experiment, the pulmonary functions of the mice from each group of Example 5 were evaluated with Unrestrained Whole Body Plethysmography (WBP). The inspiratory and expiratory flow rates of mice were calculated by measuring changes in the air inside and outside of a specific chamber, and respiratory parameters can be obtained therefrom. The respiratory parameters comprise the peak inspiratory flow (PIF) (i.e., the maximal volume being inspired in a period of time), peak expiratory flow (PEF) (i.e., the maximal volume being expired in a period of time), inspiratory time (Ti) (i.e., the average time of inspiration in a period of time), expiratory time (Te) (i.e., the average time of expiration in a period of time), respiratory rate (RR) (i.e., the numbers of breath per minute), accumulated volume (AV) (i.e., the average volume of air being breathed per minute), tidal volume (TV) (i.e., the average volume of air being expired per time), relaxation time (RT) (i.e., the average time needed for raising the pressure of air hatch to 40% of the maximal value), etc. The results are shown in FIG. 8.

As shown in FIG. 8, as compared to the "oil group," mice from the "low-dose group" and "high-dose group" had significantly decreased ($p<0.05$) expiratory time and relaxation time, and a significantly increased ($p<0.01$) accumulated volume. Besides, the other respiratory parameters of the "low-dose group" and "high-dose group" were also closer to the control group (normal mice).

The above results show that the compound of formula (I) of the present invention can effectively maintain the pulmonary function of mice and alleviate the Bleomycin sulfate-induced decrease in pulmonary function.

Example 7: Observation of Tissue Slice

In the process of pulmonary fibrosis, fibrous substances (e.g., extracellular matrix components such as collagen, elastin and fibronectin) will gradually occupy the pulmonary interstitial tissue, leading to thickening of alveolar wall tissue. Therefore, the experiment as follow was conducted to ascertain whether the compound of formula (I) of the present invention can effectively delay or alleviate the phenomenon of pulmonary fibrosis as described above.

After completing the measurement of the pulmonary function in Example 6, the mice were sacrificed. Pulmonary tissue samples were taken from the mice, and separated into two groups (each group comprised samples from the control group, oil group, low-dose group and high-dose group). One of the two groups was preserved at −20° C. for the follow-up experiment, and the other group was analyzed by hematoxylin-sosin stain (H&E stain). The results are shown in FIG. 9.

Figure 9:
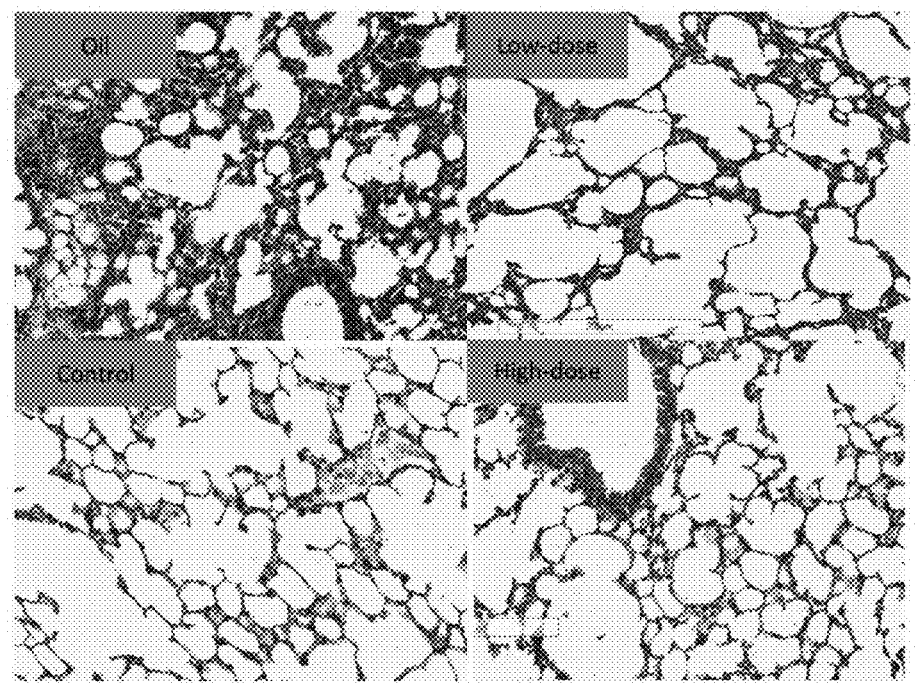
FIG. 9 is a photograph showing histopathology findings in the lungs of mice injected with Bleomycin sulfate and administrated with compound (1), wherein the H&E stain results of the control group, low-dose group, high-dose group and oil group are shown.
Figure 10:
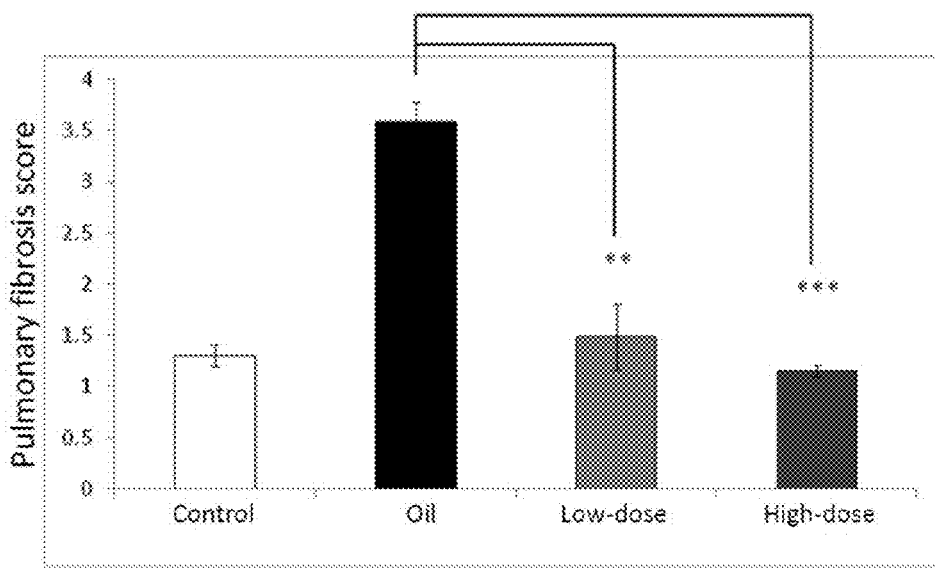
FIG. 10 is a bar diagram showing the histopathology findings in the lungs of mice injected with Bleomycin sulfate and administrated with compound (1), wherein the pulmonary fibrosis scores of mice from the control group, low-dose group, high-dose group and oil group are shown ("*" represents a P value<0.01, showing that there is a significant difference between different groups; "***" represents a P value<0.001, showing that there is a significant difference between different groups)

Furthermore, to further observe the fibrosis conditions of mice lung tissue, the method for scoring the pulmonary fibrosis described in the Ashcroft et al.'s literature was used to score the results shown in FIG. 9 (from 0 to 8), wherein a higher score represents a more severe condition of pulmonary fibrosis. The results are shown in FIG. 10. The scoring method as mentioned above can be seen in, for example, Simple method of estimating severity of pulmonary fibrosis on a numerical scale. *J Clin Pathol.* 1988 April; 41(4): 467-70, which is incorporated herein in its entirety by reference.

As shown in FIG. 9, as compared to the mice from the "control group," the alveolar wall tissue of mice from the "oil group" became significantly thicker, and the pulmonary cells of those mice exhibited a significant level of abnormal infiltration, showing an abnormal proliferation of pulmonary immunocytes and fibroblasts. However, as compared to the mice from the "oil group," the alveolar wall tissues of mice from the "low-dose group" and "high-dose group" were significantly thinner, and the levels of abnormal infiltration were also significantly less. The above results illustrate that Bleomycin sulfate can lead to the abnormal proliferation of pulmonary immunocytes and fibroblasts, resulting in pulmonary fibrosis. While using the compound of formula (I) of the present invention can effectively delay or alleviate the conditions of pulmonary fibrosis as mentioned above.

As shown in FIG. 10, as compared to mice from the "control group," the pulmonary fibrosis scores of mice from the "oil group" significantly increased. However, as compared to mice from the "oil group," the pulmonary fibrosis scores of mice from the "low-dose group" and the "high-dose group" significantly decreased.

The above results illustrate again that using the compound of formula (I) of the present invention can effectively delay or alleviate the conditions of pulmonary fibrosis as mentioned above.

Example 8: Analysis of Proteins and Total RNAs of the Pulmonary Tissue

As mentioned above, the activation of the TGF-β/Smad signaling pathway and immune overreaction in lung tissue are closely related to the onset of pulmonary fibroblasts. It is believed that, if the activation of the TGF-β/Smad signaling pathway in the lungs can be inhibited and immune reaction can be regulated, the immune overreaction produced by the lungs can be effectively inhibited, and thus the effect of delaying the onset of pulmonary fibrosis can be achieved. Furthermore, increasing the expression of surfactant C can inhibit the activation of the TGF-β/Smad signaling pathway. This Example is used to ascertain whether the compound of formula (I) of the present invention can effectively regulate the immune reaction in the pulmonary tissue and delay the onset of pulmonary fibrosis.

Figure 11:
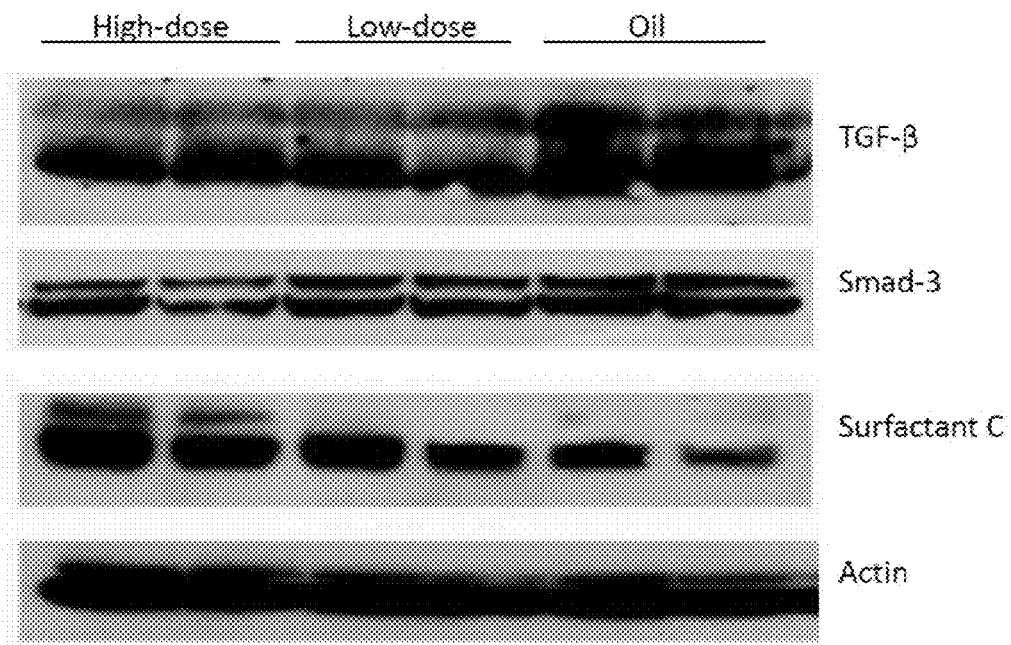
FIG. 11 is a photograph showing the expressions of TGF-β protein, smad3 protein, and surfactant C in the pulmonary tissue samples of mice, wherein the expression results were analyzed by western blotting, and the results of the high-dose group, low-dose group and oil group are shown.

The samples of mice pulmonary tissue provided by Example 7 and preserved at −20° C. were removed from storage, and then ground in liquid nitrogen. Thereafter, the proteins from a portion of ground samples of each group were extracted using a PRO-PREP™ Protein extraction Kit. The expressions of TGF-β protein, smad3 protein and surfactant C in the samples of each group were measured with western blotting, wherein the actin served as an internal control. The results are shown in FIG. 11.

Figure 12:
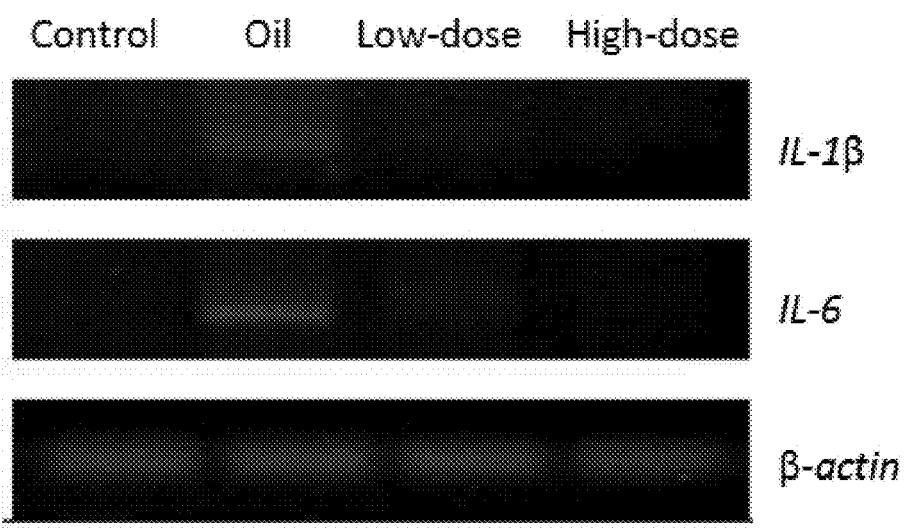
FIG. 12 is a photograph showing the expressions of immunity-related genes IL-β and IL-6 in the pulmonary tissue samples of mice, wherein the expression results were analyzed by RT-PCR, and the results of the control group, oil group, low-dose group and high-dose group are shown.

Then, for another portion of ground samples of each group, the total RNAs were extracted using an RNeasy Mini Kit. The QuantiTect Reverse Transcription Kit was used to conduct reverse transcription on the total RNA to obtain the cDNA. Thereafter, RT-PCR was conducted on the cDNA to analyze the mRNA expression levels of immune-related genes such as IL-β and IL-6 for each group, wherein β-actin served as an internal control. The results of the control group served as the basis for calculating the relative expression levels of the other groups. The results are shown in FIG. 12 and Table 8.

TABLE 8

| Group | Relative expression level (fold) | |
|---|---|---|
| | IL-β | IL-6 |
| Control group | 1 | 1 |
| Oil group | 2.34 | 3.26 |
| Low-dose group | 1.02 | 1.36 |
| High-dose group | 0.52 | 0.53 |

As shown in FIG. 11, as compared to the oil group, the expression levels of TGF-β protein and smad3 protein in the low-dose group and the high-dose group were both significantly lower, while the expression levels of surfactant C in the low-dose group and the high-dose group were significantly higher. The above results show again that the compound of formula (I) of the present invention can inhibit the activation of the TGF-β/Smad signaling pathway.

As show in FIG. 12 and Table 8, as compared to the control group, the mRNA expressions of IL-β and IL-6 genes in the oil group both significantly increased. However, as compared to the oil group, the mRNA expressions of immune-related genes such as IL-β and IL-6 in the low-dose group and the high-dose group significantly decreased. The above results illustrate that the compound of formula (I) of the present invention has the effect of regulating the immune response in the pulmonary tissue, inhibiting the immune overreaction produced by the lungs, and thus the compound of formula (I) can be used to delay the onset of pulmonary fibrosis.

As shown in the above in vitro and in vivo experiments, the compound of formula (I) of the present invention has the effects of enhancing the anti-oxidation capability of alveolar cells, increasing the survival rate of alveolar cells, alleviating oxidative stress-induced injury to the pulmonary tissue, inhibiting pulmonary fibroblast to myofibroblast conversion, inhibiting the epithelial-mesenchymal transition (EMT) of pulmonary fibroblasts and inhibiting the overexpression of extracellular matrix. Moreover, the compound of formula (I) can effectively regulate the immune response in pulmonary tissue, alleviate the thickening of alveolar wall tissue, alleviate the abnormal infiltration of pulmonary cells and/or alleviate the decrease in pulmonary function, and thus can be used to delay the onset of pulmonary fibrosis and/or treat pulmonary fibrosis.

BRIEF DESCRIPTION OF REFERENCE NUMERALS

Not applicable.

What is claimed is:

1. A method of delaying the onset of idiopathic pulmonary fibrosis or treating idiopathic pulmonary fibrosis, comprising administering to a subject in need an effective amount of an active ingredient selected from the group consisting of a synthesized compound of formula (I), a pharmaceutically acceptable salt of the synthesized compound of formula (I), and combinations thereof:

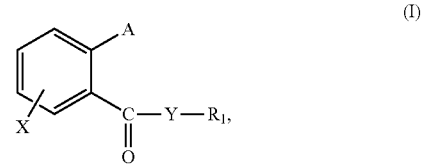

wherein,
when A is

X is H, Y is O, $R_1$ is absent, and Y and A bind together to form a five-membered ring; and
when A is

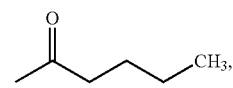

X is H, Y is O, and $R_1$ is H.

2. The method as claimed in claim 1, wherein the synthesized compound of formula (I) is the following compound (1):

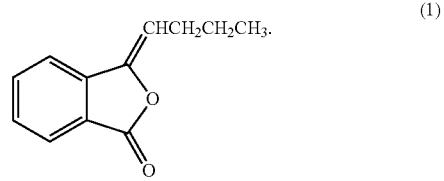

3. The method as claimed in claim 1, wherein the synthesized compound of formula (I) is the following compound (2):

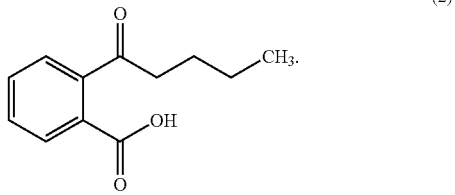

(2)

4. The method as claimed in claim 1, which is for enhancing the anti-oxidation capability of alveolar cells, increasing the survival rate of alveolar cells, alleviating the oxidative stress-induced injury to the pulmonary tissue, inhibiting the pulmonary fibroblast to myofibroblast conversion, inhibiting the epithelial-mesenchymal transition of pulmonary fibroblasts and/or inhibiting the overexpression of extracellular matrix.

5. The method as claimed in claim 1, which is for regulating the immune response in pulmonary tissue, alleviating the thickening of alveolar wall tissue, alleviating the abnormal infiltration of pulmonary cell and/or alleviating the decrease in pulmonary function.

6. The method as claimed in claim 1, which is for regulating the expression of Sox2 protein in cells, inhibiting the expression of collagen and inhibiting the expression of TGF-β protein.

7. The method as claimed in claim 1, wherein the active ingredient is administered at an amount ranging from about 1 mg/kg-body weight to about 500 mg/kg-body weight per day.

8. The method as claimed in claim 1, wherein the active ingredient is administered at an amount ranging from about 5 mg/kg-body weight to about 200 mg/kg-body weight per day.

9. The method as claimed in claim 1, wherein the active ingredient is administered at an amount ranging from about 10 mg/kg-body weight to about 100 mg/kg-body weight per day.

10. The method as claimed in claim 2, which is for enhancing the anti-oxidation capability of alveolar cells, increasing the survival rate of alveolar cells, alleviating the oxidative stress-induced injury to the pulmonary tissue, inhibiting the pulmonary fibroblast to myofibroblast conversion, inhibiting the epithelial-mesenchymal transition of pulmonary fibroblasts and/or inhibiting the overexpression of extracellular matrix.

11. The method as claimed in claim 2, which is for regulating the immune response in pulmonary tissue, alleviating the thickening of alveolar wall tissue, alleviating the abnormal infiltration of pulmonary cell and/or alleviating the decrease in pulmonary function.

12. The method as claimed in claim 2, which is for regulating the expression of Sox2 protein in cells, inhibiting the expression of collagen and inhibiting the expression of TGF-β protein.

13. The method as claimed in claim 2, wherein the active ingredient is administered at an amount ranging from about 1 mg/kg-body weight to about 500 mg/kg-body weight per day, and wherein the active ingredient is compound (1).

14. The method as claimed in claim 3, which is for enhancing the anti-oxidation capability of alveolar cells, increasing the survival rate of alveolar cells, alleviating the oxidative stress-induced injury to the pulmonary tissue, inhibiting the pulmonary fibroblast to myofibroblast conversion, inhibiting the epithelial-mesenchymal transition of pulmonary fibroblasts and/or inhibiting the overexpression of extracellular matrix.

15. The method as claimed in claim 3, which is for regulating the immune response in pulmonary tissue, alleviating the thickening of alveolar wall tissue, alleviating the abnormal infiltration of pulmonary cell and/or alleviating the decrease in pulmonary function.

16. The method as claimed in claim 3, which is for regulating the expression of Sox2 protein in cells, inhibiting the expression of collagen and inhibiting the expression of TGF-β protein.

17. The method as claimed in claim 3, wherein the active ingredient is administered at an amount ranging from about 1 mg/kg-body weight to about 500 mg/kg-body weight per day, and wherein the active ingredient is compound (2).

18. The method as claimed in claim 1, wherein the active ingredient is administered by an oral or parenteral route of administration.

* * * * *